United States Patent
Tondeur et al.

[11] Patent Number: 5,962,334
[45] Date of Patent: Oct. 5, 1999

[54] PROCESS FOR EXTRACTING 2,3,7,8-TETRACHLORODIBENZO-P-DIOXIN

[75] Inventors: Yves G. Tondeur, Chapel Hill; Phillip W. Albro, Cary; Michael D. Chu, Durham, all of N.C.

[73] Assignee: Triangle Laboratories, Inc., Durham, N.C.

[21] Appl. No.: 08/555,565

[22] Filed: Nov. 8, 1995

[51] Int. Cl.[6] .................................................. G01N 1/34
[52] U.S. Cl. ........................... 436/178; 436/93; 436/125; 436/126; 436/161; 436/173
[58] Field of Search .................... 436/178, 161, 436/173, 93, 126, 125

[56] References Cited

U.S. PATENT DOCUMENTS

| | | | |
|---|---|---|---|
| 4,238,472 | 12/1980 | Albro et al. | 424/1 |
| 4,798,807 | 1/1989 | Vanderlaan et al. | 436/548 |
| 5,128,244 | 7/1992 | Poland et al. | 435/7.8 |
| 5,149,444 | 9/1992 | Hoch | 210/751 |
| 5,429,925 | 7/1995 | Vanderlaan et al. | 435/7.1 |
| 5,492,838 | 2/1996 | Pawliszyn | 436/178 |
| 5,512,491 | 4/1996 | Mehkeri et al. | 436/177 |

OTHER PUBLICATIONS

Fireston et al., J. Ass. Offic. Anal. Chem. (1972), vol. 55, No. 1, pp. 85–92.

Baughman et al., Advances in Chemistry Series 120, E. Blair, Ed., American Chemical Society: Washington, D.C. (1973), pp. 92–104.

Baughman et al., Environmental Health Perspectives (1973), Experimental Issue No. 5, pp. 27–35.

Patterson et al., Chemosphere (1989), vol. 19, No. 1–6, pp. 89–96.

Turner et al., Adv. Lab. Auto. Rob. (1990), pp. 171–184.

Chang et al., Anal. Chem. (1993), vol. 65, No. 18, pp. 2420–2427.

Soyfer et al., Organohalogen Compounds (1993), pp. 79–81.

Hass et al., Anal. Chem., vol. 50, No. 11, pp. 1474–1479 (1978).

*Primary Examiner*—Jan Ludlow
*Attorney, Agent, or Firm*—Charles W. Calkins; Kilpatrick Stockton LLP

[57] ABSTRACT

A process for the extraction and purification of TCDD (2,3,7,8-Tetrachlorodibenzo-p-dioxin) from a sample matrix. The process of the present invention overcomes a problem of prior art processes for extracting TCDD, by providing for chemical destruction of potentially interfering components in a sample matrix making the steam distillation of TCDD possible. A typical sample matrix comprises blood serum.

17 Claims, 2 Drawing Sheets

PROCESS FOR EXTRACTING 2,3,7,8-TETRACHLORODIBENZO-P-DIOXIN

FIELD OF THE INVENTION

The present invention relates to a process for extracting 2,3,7,8-Tetrachlorodibenzo-p-dioxin from a sample matrix, preferably a biological fluid such as blood. The invention advantageously provides a process which achieves higher yields in shorter times than previous processes.

BACKGROUND 2,3,7,8-Tetrachlorodibenzo-p-dioxin (hereinafter referred to as TCDD) is generally recognized as a toxic member of a family of compounds that occur as inadvertent environmental contaminants. The suspected and/or known health effects of these compounds are so severe that analytical methods for their determination in human blood serum need to reach parts-per-quadrillion ($10^{-15}$) levels (femtograms per milliliter of serum). Presently utilized processes are both slow and expensive, because of the difficulty in extracting such small amounts of TCDD with reasonable recovery and the tedious nature of the processes used to remove materials other than TCDD that interfere with analysis.

In prior art processes, the extraction of TCDD from blood serum and removal of interfering contaminants are generally performed as separate steps, typically requiring from several hours to several days to accomplish. Prior attempts to simultaneously extract and purify TCDD from biological fluids have been unable to provide a TCDD precursor which did not require additional, tedious purification, because of the simultaneous extraction of other biological components and contaminants.

SUMMARY OF THE INVENTION

The present invention provides a process for the extraction and purification of TCDD (2,3,7,8-Tetrachlorodibenzo-p-dioxin) from an aqueous sample matrix. A preferred aqueous sample matrix is blood, more preferably blood serum.

The process of the present invention overcomes a problem of prior art processes for extracting TCDD, by providing a means for chemical destruction of potentially interfering components in a sample matrix, such as blood serum. The chemical destruction occurs as a part of the overall extraction process and thus the chemical destruction does not increase the time requirement. In a preferred embodiment of the process of the present invention, a means for quantification of the recovered TCDD with automatic correction for recovery is provided through incorporation of an internal standard (reference compound) in such a way that recovery is not compromised.

According to the process of the present invention a high percentage of the TCDD in an aqueous sample matrix is transferred into a small volume of organic solvent through a vapor/liquid exchange process. While the exchange and transfer are occurring, a portion of the potentially interfering substances in the aqueous sample matrix are converted to non-interfering materials through reaction with a general catalyst of hydrolytic reactions. In a preferred embodiment, introduction of a reference standard into the serum is done in such a manner as to facilitate the subsequent transfer of TCDD out of its association with serum constituents.

The process of the present invention permits the preparation of extracted and interference-depleted TCDD from samples of serum in less than one hour. Since many samples can be being processed in duplicate arrangements at the same time, one person can prepare several samples for analytical determination during each hour of working time.

The process of the present invention advantageously results in a higher recovery of TCDD from aqueous samples than heretofore commonly utilized processes.

The process of the present invention may be advantageously utilized for rapid, simultaneous extraction and purification of 2,3,7,8-Tetrachlorodibenzo-p-dioxin from small samples.

Another advantage of the process of the present invention is that it is simple and economical.

A further advantage of the process of the present invention is that the high recovery permits subsequent analytical measurements to be made with maximum sensitivity.

Another advantage of the process of the present invention is that sample preparation is completed in a short period of time.

Further details and advantages of the process of the present invention will become apparent from the following more detailed descriptions.

BRIEF DESCRIPTION OF THE DRAWING

FIG. 2A shows the detector response to the TCDD, while FIG. 2B shows the response to the reference (internal) standard.

DETAILED DESCRIPTION OF THE INVENTION

Figure 1:
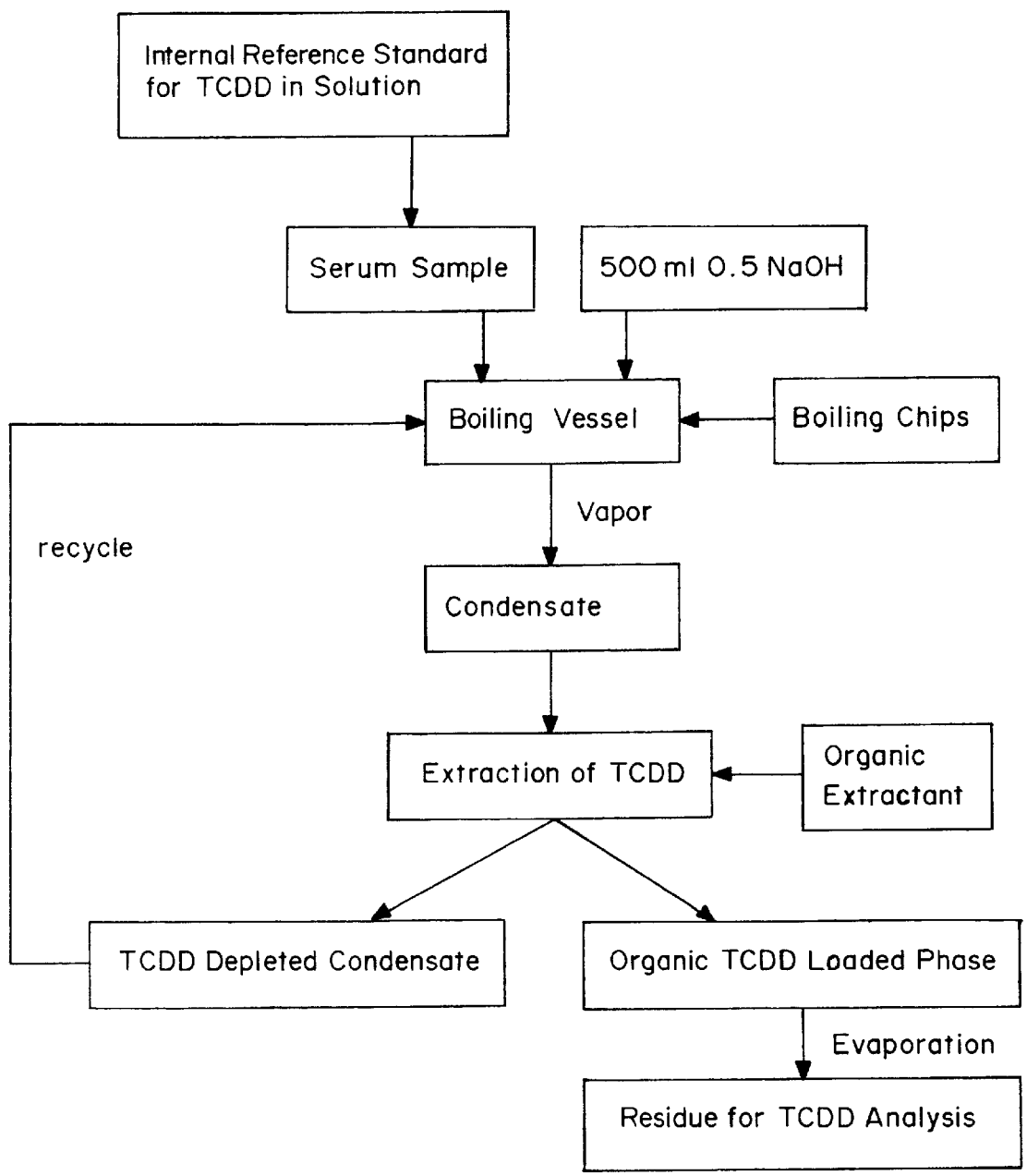
FIG. 1 is a schematic diagram of an embodiment of the process of the present invention.

According to the present invention, a process for extracting 2,3,7,8-Tetrachlorodibenzo-p-dioxin (TCDD) from an aqueous sample matrix comprises:

diluting the aqueous sample matrix with a diluent;

reacting the diluted aqueous sample matrix with a chemically active substance;

boiling the resulting aqueous sample matrix to produce vapors;

condensing said vapors to form a condensate;

contacting said condensate with an extractant for TCDD to extract TCDD and produce an extractant phase comprising TCDD, and a condensate phase depleted in TCDD, wherein the contacting of said condensate is carried out away from said aqueous sample matrix and said extractant is substantially immiscible with said condensate; and separating said extractant phase from said condensate phase, said extractant phase being sufficiently pure for analytical determination of the TCDD content.

The levels (concentration) of TCDD in the TCDD loaded extractant phase may be determined by standard analytical techniques.

The diluting and reacting steps in the process of the present invention may be combined by adding the chemically active substance to the diluent to produce a diluent composition which is added to and reacts with the aqueous sample matrix. According to this embodiment of the process of the present invention a process for extracting 2,3,7,8-Tetrachlorodibenzo-p-dioxin (TCDD) from an aqueous sample matrix comprises:

diluting the aqueous sample matrix with a diluent composition comprising a diluent and a chemically active substance which will react with the aqueous sample matrix;

boiling the resulting aqueous sample matrix to produce vapors;

condensing said vapors to form a condensate;

contacting said condensate with an extractant for TCDD to extract TCDD and produce an extractant phase comprising TCDD, and a condensate phase depleted in TCDD, wherein the contacting of said condensate is carried out away from said aqueous sample matrix and said extractant is substantially immiscible with said condensate; and separating said extractant phase from said condensate phase, said extractant phase being sufficiently pure for analytical determination of the TCDD content.

In a preferred embodiment of the process of the present invention, an internal reference standard is utilized to enable the amount of TCDD in the initial aqueous sample to be more accurately determined. According to this preferred embodiment, a process for extracting 2,3,7,8-Tetrachlorodibenzo-p-dioxin (TCDD) from an aqueous sample matrix comprises:

- adding an internal reference standard solution to said aqueous sample matrix;
- diluting the resulting aqueous sample matrix including said internal reference standard including with a diluent;
- reacting the diluted aqueous sample matrix with a chemically active substance;
- boiling the resulting aqueous sample matrix to produce vapors;
- condensing said vapors to form a condensate;
- contacting said condensate with an extractant for TCDD to extract TCDD and the internal reference standard from said condensate and produce an extractant phase comprising TCDD and the internal reference standard, and a condensate phase depleted in TCDD and the internal reference standard, wherein the contacting of said condensate is carried out away from said aqueous sample matrix and said extractant is substantially immiscible with said condensate; and
- separating said extractant phase from said condensate phase, said extractant phase being sufficiently pure for analytical determination of the TCDD content.

The levels (concentrations) of TCDD and the internal reference standard in the TCDD loaded extractant phase may be determined by standard analytical techniques, for example an iosotope dilution assay. The initial concentration of TCDD in the aqueous sample matrix may then be calculated using the internal reference standard extracted from the aqueous sample matrix.

The diluting and reacting steps of this preferred embodiment of the process of the present invention may be combined by adding the chemically active substance to the diluent to produce a diluent composition which is added to and reacts with the aqueous sample matrix. In this embodiment of the process of the present invention a process for extracting 2,3,7,8-Tetrachlorodibenzo-p-dioxin (TCDD) from an aqueous sample matrix comprises:

- adding an internal reference standard solution to said aqueous sample matrix;
- diluting the aqueous sample matrix including said internal reference standard with a diluent composition comprising a diluent and a chemically active substance which will react with the aqueous sample matrix;
- boiling the resulting aqueous sample matrix to produce vapors;
- condensing said vapors to form a condensate;
- contacting said condensate with an extractant for TCDD to extract TCDD and the internal reference standard from said condensate and produce an extractant phase comprising TCDD and the internal reference standard, and a condensate phase depleted in TCDD and the internal reference standard, wherein the contacting of said condensate is carried out away from said aqueous sample matrix and said extractant is substantially immiscible with said condensate; and
- separating said extractant phase from said condensate phase, said extractant phase being sufficiently pure for analytical determination of the TCDD content.

A preferred aqueous sample matrix is blood, more preferably blood serum, hereafter referred to as serum. The serum may be human or of other animal origin. Generally, the starting amount of aqueous sample matrix will range from 1 to 10 milliliters, more typically from 2 to 4 milliliters.

Diluents suitable for use in the process of the present invention include, but are not limited to water and water based solutions.

The chemically active substance utilized in the process of the present invention is preferably a substance which will aid in the destruction of sample matrix components which would otherwise interfere with the release of TCDD into the vapor phase during boiling, and/or subsequent extraction of TCDD from the condensate. The chemically active substance should preferably increase the hydroxide ion concentration in the aqueous sample matrix (impart alkalinity) preferably in an amount at least equivalent to 0.5N sodium hydroxide, but not stronger than 2N sodium hydroxide in ability to promote base-catalyzed hydrolysis. Suitable chemically active substances include, but are not limited to, an alkali hydroxide, such as sodium hydroxide, potassium hydroxide, cesium hydroxide, or lithium hydroxide. A preferred chemically active substance is 1N potassium hydroxide.

The chemically active substance may be added to the diluent prior to its addition to the aqueous sample matrix to form a diluent composition which is utilized to dilute and react with the aqueous sample matrix. The amount of diluent composition utilized in the process of the present invention should be an amount sufficient to permit the extraction of TCDD from the aqueous sample matrix. Generally, 100 to 250 milliliters (mL) of diluent composition is utilized per mL of aqueous sample matrix.

Alternatively, the diluent and chemically active substance may be sequentially added to the aqueous sample matrix. In this case, the total volume of diluent and chemically active substance would also equal 100 to 250 milliliters (mL) of diluent composition per mL of aqueous sample matrix.

The internal reference standard solution comprises:

- 0.1 to 100 picograms, preferably 1 to 15 picograms, more preferably about 10 picograms of an internal reference standard for TCDD per millimeter of the sample matrix and
- less than or equal to 100 microliters, preferably 1 to 15 microliters, more preferably about 10 microliters of a water-miscible, hydrogen bonding solvent;

wherein the internal reference standard for TCDD is dissolved in the solvent. Suitable internal reference standards for TCDD include, but are not limited to, an isotopically labeled analog of TCDD such as $^{13}C_{12}$-2,3,7,8-TCDD; $^{37}Cl_4$-2,3,7,8-TCDD; $^{13}C_6$-2,3,7,8-TCDD. Suitable water-miscible, hydrogen bonding solvents include, but are not limited to, methanol, DMSO, acetone, ethanol.

As set forth above, the internal reference standard for TCDD may be added to the aqueous sample matrix prior to the dilution of the aqueous sample matrix. In certain cases, an internal reference standard for TCDD may already be present in the aqueous sample matrix and therefore an internal reference standard for TCDD would not need to be added to the aqueous sample matrix.

The addition of an internal reference standard for TCDD to the aqueous sample matrix, the dilution of the aqueous sample matrix and the reacting of the aqueous sample matrix and the chemically active substance may all be accomplished utilizing standard laboratory equipment and techniques. When necessary, these steps may be carried out while the aqueous sample matrix is under agitation or being stirred. In a preferred embodiment of the process of the present invention, the aqueous sample matrix containing an internal reference standard is combined with a diluent composition including a chemically active agent in a flask or vessel which will be utilized to boil the resulting aqueous sample matrix.

The boiling of the resulting aqueous sample matrix to produce vapors may be carried out utilizing standard laboratory equipment and techniques. Generally the resulting aqueous sample matrix is heated in a vessel or flask utilizing a hot plate or other heating element to generate vapors (a vapor phase). A suitable number of ebullition promoting materials commonly known as "boiling chips" or "boiling stones" may be added to promote the generation of vapors. Such chips or stones may be of any type commonly used for such purpose, including but not limited to porcelain, carborundum, or glass.

Condensation of the vapor phase (vapors) may be accomplished by capturing the vapors and allowing the vapors to cool to produce a condensate. In the process of the present invention, after the condensate is contacted with an extractant for TCDD, the TCDD depleted condensate may be recycled back into the boiling aqueous sample matrix.

The extractant for TCDD utilized in the process of the present invention is an extractant which is substantially immiscible with water and capable of extracting TCDD from an aqueous solution comprising TCDD to produce an extractant phase comprising TCDD. The extractant for TCDD should also be capable of extracting the internal reference standard, and loading the internal reference standard into the extractant phase, in processes where an internal reference standard is utilized. The extractant for TCDD should generally have a boiling point of 90° C. or greater, preferably of 100° C. or greater, so that the extractant does not evaporate at the temperatures where the process is conducted. Any extractant meeting these criteria will generally be suitable for use in the process of the present invention. Suitable extractants include, but are not limited to: 9-carbon containing hydrocarbon solvents (e.g., nonane), isooctane, toluene and tridecane.

The extraction steps of the process of the present invention may be performed utilizing commercially available standard laboratory equipment, including condensers and generally available steam distillation equipment.

An embodiment of the process of the present invention is depicted schematically in FIG. 1. With reference to FIG. 1, in an embodiment of the process of the present invention an Internal Reference Standard for TCDD in solution is added to a blood serum sample. The internal reference standard containing serum sample, and a diluent composition comprising NaOH as a chemically active substance are admixed in a boiling vessel. A suitable number of "boiling chips" or "boiling stones" are added, the number being unspecified but commonly familiar to anyone generally experienced with the simple art of distillation to the boiling vessel.

The boiling vessel is connected to an apparatus, such as those commercially available, that permits the solution in the boiling vessel to be boiled to produce vapors. The vapors generated comprise TCDD and the internal reference standard and are captured and condensed to form a condensate. The condensate passes through an organic extractant for TCDD which is substantially immiscible with the condensate. The organic extractant dissolves and extracts TCDD and the internal reference standard from the condensate to produce an extract phase loaded with TCDD and the internal reference standard, and a TCDD (and internal reference standard) depleted condensate. The depleted condensate is recycled to the boiling vessel. The organic extractant selected is one which does not evaporate from the apparatus during the application of heat to the boiling vessel. In addition the organic extractant does not enter the vessel in which boiling proceeds.

Suitable apparatuses for conducting the depicted process are widely available from suppliers of laboratory glassware and include those known to those of ordinary skill in the art of steam distillation.

According to the process of the present invention, boiling of the diluted serum solution containing internal standard and chemically active substances is continued until the TCDD has been transferred into the organic extractant to an extent acceptable to the operator. In the interests of rapid sample processing this time should not exceed one hour, and is primarily determined by the rate at which heat is applied to the containment vessel. A typical time of boiling would be 45 minutes.

At the end of the boiling period heat is no longer applied to the boiling vessel. The organic extractant is removed from the apparatus and concentrated by evaporation to an amount appropriate for its utilization in whatever analytical determination procedure is selected. Concentration of the organic solvent containing TCDD may be accomplished by any conventional means, including but not limited to the use of an evaporator, steam bath, or the like.

Analytical determination of the TCDD in the organic solvent derived from the described procedure may be performed by any means offering adequate sensitivity and specificity.

The features and advantages of the process of the present invention are further illustrated by the following example.

EXAMPLE

An embodiment of the process of the present invention was performed to illustrate the advantageous recovery of TCDD from a 2 mL human blood serum sample having a known concentration of TCDD of 500 femtograms of TCDD per milliliter.

An internal reference standard for TCDD, which in this example was a 0.02 mL solution of 2 picograms of $^{13}C_{12}$-2,3,7,8-TCDD in methanol, was added to the 2 mL serum sample. 500 mL of 1.0N NaOH diluent solution, comprising NaOH as a chemically active substance were admixed with the internal reference standard containing serum sample in a 1-Liter boiling vessel suitable for reflux or distillation conditions. 6 to 8 carborundum "boiling chips" were also added to the boiling vessel.

The boiling vessel containing the admixed solution was connected to a commercially available microsteam distillation apparatus that permitted the solution to be boiled, under such conditions that the vapors therefrom were condensed back to the liquid state to form a condensate. The condensed liquid passed through 1 mL of isooctane (an organic extractant capable of dissolving TCDD but substantially immiscible with the condensate) which extracted TCDD and the internal reference standard to form an extractant phase comprising TCDD and the internal reference standard. The TCDD depleted condensate liquid thereafter returned to the boiling vessel.

Boiling was continued for 45 minutes. At the end of the boiling period heat was no longer applied to the boiling vessel. The extractant phase comprising the TCDD and internal reference standard was removed from the apparatus and concentrated in a vacuum centrifuge.

Figure 2:
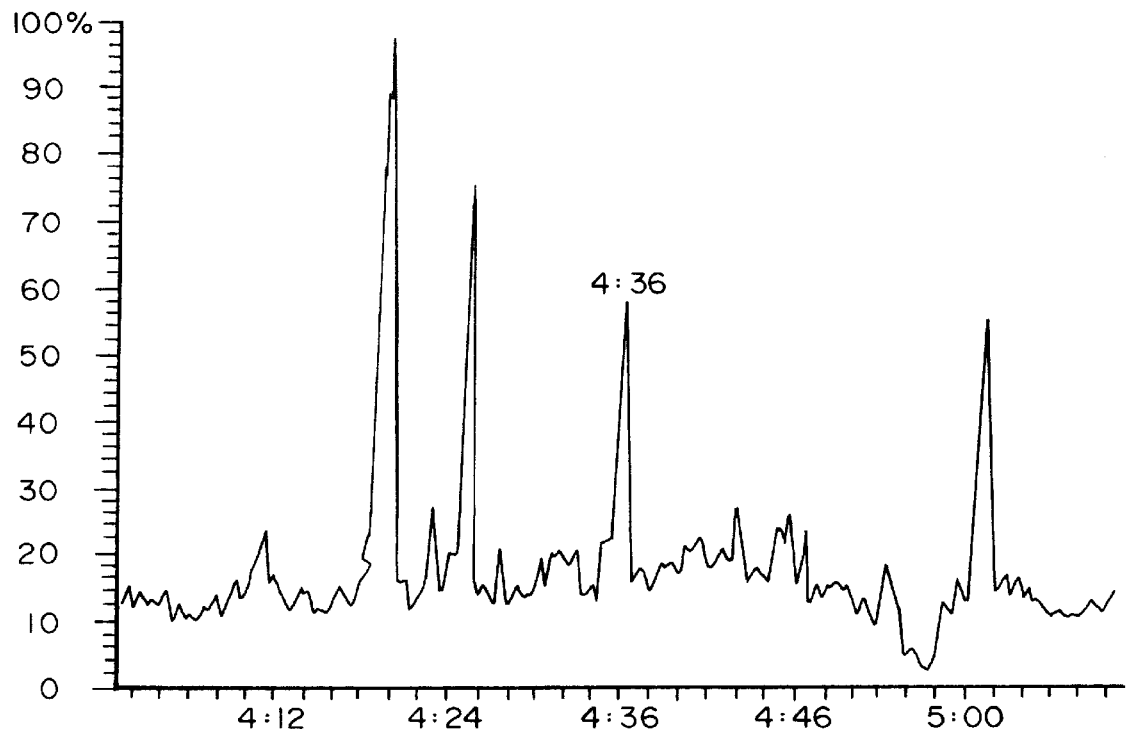
FIGS. 2A and 2B depict the appearance of selected ion monitoring mass chromatograms of a sample prepared by the manner described in the example herein.
Figure 2:
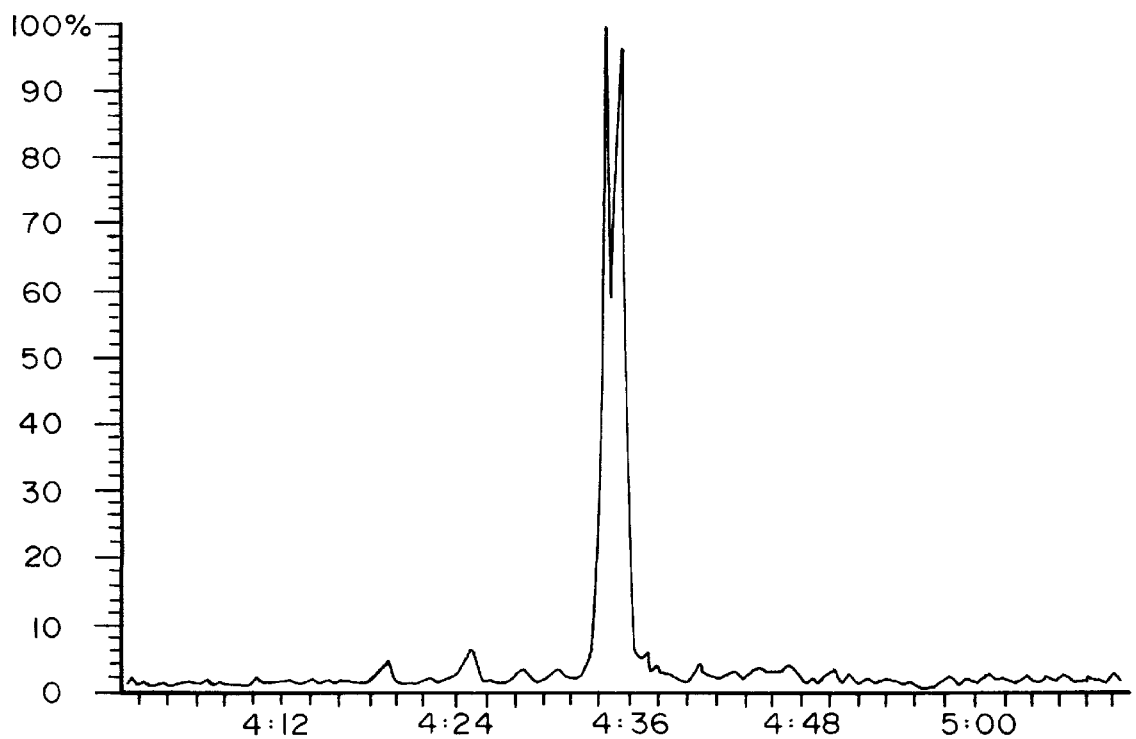

A combination of gas chromatography with mass spectrometry was utilized to generate the graphs illustrated in FIG. 2. These results illustrate that the process of the invention extracted a TCDD with sufficient recovery and degree of freedom from interferences for measurement of TCDD initially at a concentration of 0.5 parts per trillion (0.5 picograms of TCDD per gram of serum).

As described above, and shown by the example embodiment, the process of the present invention provides the following advantages: transfer of TCDD from the serum to an organic solvent in less than one hour with no additional purification of TCDD required; chemical conversion of substances typically found in serum from substances that would otherwise have co-steam distilled with the TCDD or reduced its ability to be steam distilled, into substances that do not have such properties, and the facile modification of the organic solvent solution of TCDD into a form suitable for analytical determination (quantification).

It will thus be seen that the advantages set forth, among those made apparent from the preceding description, are efficiently obtained by the process of the present invention. Since certain changes may be made in carrying out the above embodiments of the process, without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

We claim:

1. A process for extracting 2,3,7,8-Tetrachloro-dibenzo-p-dioxin (TCDD) from an aqueous sample matrix comprising:

diluting the aqueous sample matrix with a diluent to produce a diluted aqueous sample matrix;

reacting the diluted aqueous sample matrix with a chemically active substance effective to promote base-catalyzed hydrolysis to form a resulting aqueous sample matrix;

boiling the resulting aqueous sample matrix to produce vapors;

condensing said vapors to form a condensate;

contacting said condensate with an extractant for TCDD to extract TCDD and produce an extractant phase comprising TCDD and a condensate phase depleted in TCDD, wherein the contacting of said condensate is carried out away from said aqueous sample matrix and said extractant is substantially immiscible with said condensate; and separating said extractant phase from said condensate phase, said extractant phase being sufficiently pure for analytical determination of the TCDD content.

2. The process of claim 1 further comprising the step of adding an internal reference standard solution to said aqueous sample matrix prior to diluting and wherein said extractant for TCDD further extracts said internal reference standard solution to produce said extractant phase, wherein said extractant phase further comprises TCDD and said internal reference standard solution and said condensate phase is depleted in TCDD and said internal reference standard solution.

3. The process of claim 1 wherein the diluting and reacting steps are combined and comprise:

diluting the aqueous sample matrix with a diluent composition comprising the diluent and the chemically active substance, wherein said diluent composition will react with the aqueous sample matrix.

4. The process of claim 3 further comprising the step of adding an internal reference standard solution to said aqueous sample matrix prior to diluting and wherein said extractant for TCDD further extracts said internal reference standard solution to produce said extractant phase, wherein said extractant phase further comprises TCDD and said internal reference standard solution and said condensate phase is depleted in TCDD and said internal reference standard solution.

5. The process of claim 4 wherein the extractant for TCDD comprises an organic solvent capable of dissolving TCDD.

6. The process of claim 4 further comprising evaporating a portion of said extractant phase after separating said extractant phase from said condensate to produce an evaporated TCDD loaded organic phase.

7. The process of claim 6 further comprising analyzing the evaporated TCDD loaded organic phase for TCDD concentration level.

8. The process of claim 1 wherein the aqueous sample matrix comprises blood serum.

9. The process of claim 8 wherein the blood serum has been pretreated with an internal reference standard for TCDD.

10. The process of claim 7 wherein the internal reference standard comprises $^{13}C_{12}$-2,3,7,8-TCDD.

11. The process of claim 10 wherein the diluent comprises water and the chemically active agent comprises 1N potassium hydroxide.

12. The process of claim 11 wherein the extractant for TCDD comprises a nine carbon containing hydrocarbon solvent.

13. The process of claim 12 further comprising adding an ebullition promoting material to the resulting aqueous matrix formed from the reaction of the blood serum and the chemically active substance.

14. A process for extracting 2,3,7,8-Tetrachlorodibenzo-p-dioxin (TCDD) from an aqueous sample matrix comprising:

adding an internal reference standard solution to said aqueous sample matrix;

diluting the aqueous sample matrix with a diluent composition comprising a diluent and a chemically active substance, wherein said diluent composition will react with the aqueous sample matrix to form a resulting aqueous sample matrix, said chemically active substance comprising a substance effective to increase hydroxide ion concentration in an amount equivalent to the increase caused by an alkali metal hydroxide to promote base-catalyzed hydrolysis;

boiling the resulting aqueous sample matrix to produce vapors;

condensing said vapors to form a condensate;

contacting said condensate with an extractant for TCDD, wherein said extractant for TCDD further extracts said internal reference standard solution to produce an extractant phase comprising TCDD and said internal reference standard solution and a condensate phase depleted in TCDD and said internal reference standard solution, and wherein the contacting of said condensate is carried out away from said aqueous sample matrix and said extractant is substantially immiscible with said condensate; and separating said extractant phase from said condensate phase, said extractant phase being sufficiently pure for analytical determination of the TCDD content.

15. A process for extracting 2,3,7,8-Tetrachlorodibenzo-p-dioxin (TCDD) from blood serum comprising:

pretreating said blood serum with an internal reference standard for TCDD comprising $^{13}C_{12}$-2,3,7,8-TCDD;

diluting the blood serum with water to produce a diluted blood serum;

reacting the diluted blood serum with 1N potassium hydroxide to form a resulting blood serum;

boiling the resulting blood serum to produce vapors;

condensing said vapors to form a condensate;

contacting said condensate with an extractant for TCDD to extract TCDD and produce an extractant phase comprising TCDD and a condensate phase depleted in TCDD, wherein the contacting of said condensate is carried out away from said aqueous sample matrix and said extractant is substantially immiscible with said condensate; and separating said extractant phase from said condensate phase, said extractant phase being sufficiently pure for analytical determination of the TCDD content.

16. The process of claim 15, wherein the extractant for TCDD comprises an eight carbon containing hydrocarbon solvent.

17. The process of claim 16, further comprising adding an ebullition promoting material to the resulting blood serum formed from the reaction of the blood serum and the chemically active substance.

* * * * *